United States Patent [19]

Oakes et al.

[11] Patent Number: 5,422,028
[45] Date of Patent: Jun. 6, 1995

[54] PEROXYACIDS

[75] Inventors: John Oakes, Darnhall Winsford; David W. Thornthwaite, Neston South Wirral, both of Great Britain

[73] Assignee: Lever Brothers Company, Division of Conopco, Inc., New York, N.Y.

[21] Appl. No.: 210,973

[22] Filed: Mar. 21, 1994

[30] Foreign Application Priority Data

Mar. 22, 1993 [GB] United Kingdom ............... 9305863

[51] Int. Cl.$^6$ ..................... C01B 15/055; C11D 7/54; C07C 409/00
[52] U.S. Cl. ................. 252/102; 252/186.38; 252/186.42; 252/95; 562/2; 562/4
[58] Field of Search ............ 562/2, 4; 252/186.38, 252/186.42, 95, 102

[56] References Cited

U.S. PATENT DOCUMENTS

| | | | |
|---|---|---|---|
| 4,634,551 | 1/1987 | Burns et al. | 252/102 |
| 5,098,598 | 3/1992 | Sankey et al. | 252/786.42 |
| 5,158,700 | 10/1992 | Sotoya et al. | 252/186.38 |
| 5,245,075 | 9/1993 | Venturello et al. | 560/302 |
| 5,294,362 | 3/1994 | Venturello et al. | 252/102 |

FOREIGN PATENT DOCUMENTS 0325288 7/1989 European Pat. Off. .
0316809 11/1989 European Pat. Off. .

*Primary Examiner*—Gary Geist
*Assistant Examiner*—Joseph D. Anthony
*Attorney, Agent, or Firm*—Milton L. Honig

[57] ABSTRACT

Cationic peroxyacid are provided having formula (I):

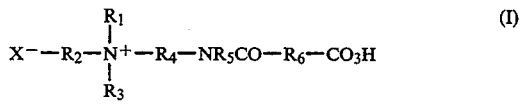

wherein:

$R_1$ is an optionally substituted $C_1$–$C_{24}$ alkyl or alkenyl or alkylaryl with a $C_1$–$C_{24}$ alkyl group;

$R_2$ and $R_3$ are each independently a $C_1$–$C_3$ alkyl or $C_1$–$C_3$ substituted alkyl group;

$R_4$ and $R_6$ are each independently aryl or $(CH_2)_n$ where n is an integer from 1 to 7;

$R_5$ is selected from hydrogen, $C_1$–$C_7$ alkyl, or aryl substituted with a $C_1$–$C_2$ alkyl; and $X^-$ is a counter anion.

These cationic peroxyacids show good bleaching activity over a wide range of pH conditions.

5 Claims, No Drawings

PEROXYACIDS

This invention relates to novel amidocationic peroxyacids and their use as bleaches and, in particular, their use as bleaches in detergent compositions used for washing fabrics.

It is well known that organic peroxyacids can be used as bleaching agents in detergent compositions. Many different types of organic peroxyacids have been proposed such as peroxybenzoic acid, peroxyphthalic acid, peroxyalkanoic and diperoxyalkanedioic acids, described in U.S. Pat. Nos. 4,110,095, 4,170,453 and 4,325,828. Other classes of peroxyacids which have been disclosed include amidoperoxyacids which contain a polar amide linkage part way along a hydrocarbon chain (U.S. Pat. Nos. 4,634,551 and 4 686 063) and phthalimido-substituted peroxyalkanoic acids (EP-A-325 288).

There is now an increasing interest in cationic organic peroxyacids, particularly for use in bleaching and detergent compositions since, when compared to their noncationic counterparts, they
i) are more substantive;
ii) have a better bleaching performance; and
iii) are pH-robust.

A range of peroxyacids comprising a quaternary ammonium group are described in European Patent Specification 316 809 (Ausimont). In particular, it discloses a range of materials of formula $$X^- \ RR_1R_2 \ N^+A \ (CO_3H)_n$$

wherein A is selected from a wide range of groups including, optionally substituted, alkylene, arylene and cycloalkylene groups; X represents $HSO_4$, $CH_3SO_3$; and n is preferably 1 or 2. The disadvantage with this type of material is that it
i) deprotonates in alkaline medium and, therefore, is less substantive and a poorer bleach; and
ii) undergoes self-decomposition reaction which renders it unstable in solution.

We have now found a related group of compounds but which contain the group NRCO, in which R is hydrogen, $C_1$-$C_7$ alkyl, or aryl substituted with a $C_1$-$C_2$ alkyl, which have good bleach activity, over a wide range of pH conditions.

Accordingly, the present invention provides cationic peroxyacids of formula (I)

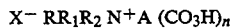

wherein:
$R_1$ is an optionally substituted $C_1$-$C_{24}$ alkyl or alkenyl or alkylaryl with a $C_1$-$C_{24}$ alkyl group;
$R_2$ and $R_3$ are each independently a $C_1$-$C_3$ alkyl or $C_1$-$C_3$ substituted alkyl group;
$R_4$ and $R_6$ are each independently aryl or $(CH_2)_n$ where n is an integer from 1 to 7;
$R_5$ is selected from hydrogen, $C_1$-$C_7$ alkyl, or aryl substituted with a $C_1$-$C_2$ alkyl; and
$X^-$ is a counter anion.

When $R_6$ is aryl, the $-CO_3H$ group is preferably in the para or meta position.

Particularly preferred cationic peroxyacids are those in which, independently,
i) $R_1$ is $C_1$-$C_{12}$, most preferably $C_1$-$C_8$, alkyl, alkenyl or alkylaryl with a $C_1$-$C_7$, most preferably $C_1$-$C_5$, alkyl group;
ii) $R_4$ is a group of formula $(CH_2)_n$ where n is an integer from 2 to 4 and most preferably is 3;
iii) $R_6$ is phenyl or $(CH_2)_{n'}$ where n' is 2 to 5 and most preferably phenyl or $(CH_2)_{n'}$ where n' is 2 to 4; and
iv) $R_5$ is hydrogen.

$X^-$ may be any suitable counter anion such as $NO_3^-$, $HSO_4^-$, $SO_4^{2-}$, $CH_3SO_4^-$ and a surfactant anions An advantage of the peroxyacids according to the present invention is that the route by which the present materials are made is simple since it involves readily available starting materials.

When $R_6$ is $(CH_2)_n$, the cationic peroxyacids of the present invention may readily be prepared by reaction of an appropriate amine with appropriate acid anhydride, in particular by reaction of an amine of formula $$R_2R_3N-R_4-NHR_5$$

with an acid anhydride of formula

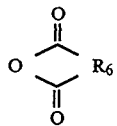

followed by quaternisation with a material comprising the group $R_1X$, and peroxidation.

When $R_6$ is phenyl, the amine is reacted with an, optionally $C_1$-$C_2$ substituted, material of formula

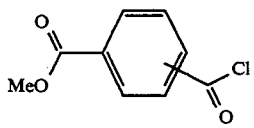

followed by quaternisation and peroxidation.

Quaternisation may be carried out, using known alkylating agents such as methyl sulphate. Peroxidation may be carried out, using hydrogen peroxide and strong acid.

The peroxyacids of the present invention may find use in a wide range of industrial applications and processes, for example, in the field of plastics as polymerisation initiators or as oxidants for olefin epoxydation, or as bleaching agents in the paper industry.

They are also particularly useful as bleaching or cleaning agents in washing, cleaning and disinfecting compositions such as laundry bleaches, hard surface cleaners, toilet bowl cleaners, automatic dishwashing compositions, denture cleaners and other sanitising compositions.

The cationic peroxyacids of the present invention find particular application in detergent compositions since they show good bleach performance at medium to low washing temperatures, that is 60° to 20° C. This means that detergent compositions containing such peroxyacids may readily be used at the medium to low wash temperatures which are becoming increasing common.

According to another aspect, the invention provides a bleaching additive composition and a bleaching detergent composition comprising an effective amount of a cationic peroxyacid of formula (I) as the bleach component.

The term "effective amount", as used herein, means the cationic peroxyacid is present in a quantity such that it is operative for its intended purpose, i.e. as a bleaching agent, when the detergent composition is combined with water to form an aqueous medium which may be used to wash and clean clothes, fabrics and other articles.

Preferably, cationic peroxyacids, when present as the bleach component, will be present in bleaching detergent compositions in amounts of from about 0.5 to 15% by weight, most preferably from 2 to 10% by weight.

Furthermore, when present as the bleach component in a bleaching additive composition, the concentration of the cationic peroxyacids will be preferably in the range of from 50 to 90% by weight.

Surfactants

The bleaching detergent compositions of the invention will contain at least one surface-active compound, which may be anionic, cationic, nonionic or amphoteric in character, present in an amount from about 3 to about 40%, preferably from 5 to 35% by weight.

Generally, mixtures of the above surface-active compounds are used. In particular, mixtures of anionic and nonionic surface-active compounds are commonly used. Amounts of amphoteric or zwitterionic surface-active compounds may also be used but this is not generally desired owing to their relatively high cost. If used, they will be present in small amounts.

The surface-active material may be naturally derived, such as soap, or a synthetic material selected from anionic, nonionic, amphoteric, zwitterionic, cationic actives and mixtures thereof. Many suitable actives are commercially available and are fully described in the literature, for example in "Surface Active Agents and Detergents", Volumes I and II, by Schwartz, Perry and Berch.

Synthetic anionic surfactants are well known to those skilled in the art. Examples include alkylbenzene sulphonates, particularly sodium linear alkylbenzene sulphonates having an alkyl chain length of $C_8$-$C_{15}$; primary ($C_{12-15}$) and secondary alkyl sulphates ($C_{14-18}$), particularly sodium $C_{12-15}$ primary alcohol sulphates; olefin sulphonates; alkane sulphonates; dialkyl sulphosuccinates; and fatty acid ester sulphonates.

It may also be desirable to include one or more soaps of fatty acids. These are preferably sodium soaps derived from naturally occurring fatty acids, for example, the fatty acids from coconut oil, beef tallow, sunflower or hardened rapeseed oil. Soaps may be incorporated in the compositions of the invention, preferably at a level of less than 25% by weight. They are particularly useful at low levels in binary (soap/anionic) or ternary mixtures together with nonionic or mixed synthetic anionic and nonionic compounds. Soaps which may be used are preferably the sodium, or, less desirably, potassium salts of saturated or unsaturated $C_{10}$-$C_{24}$ fatty acids or mixtures thereof. Typically, such soaps may be present at levels between about 0.5% and about 25% by weight, with lower levels of between about 0.5% to about 5% being generally sufficient for lather control. If the soap is present at a level between about 2% and about 20%, particularly between about 5% and about 10%, this can give beneficial detergency effects. The inclusion of soap is particularly valuable in detergent compositions to be used in hard water since the soap acts as a supplementary builder.

The preferred anionic surfactant is sodium $C_{12-15}$ primary alcohol sulphate.

Suitable nonionic detergent compounds which may be used include the reaction products of compounds having a hydrophobic group and a reactive hydrogen atom, for example, aliphatic alcohols, acids, amides or alkyl phenols with alkylene oxides, especially ethylene oxide, either alone or with propylene oxide.

Specific nonionic detergent compounds are alkyl ($C_{6-22}$) phenol-ethylene oxide condensates, the condensation products of linear or branched aliphatic $C_{8-20}$ primary or secondary alcohols with ethylene oxide, and products made by condensation of ethylene oxide with the reaction products of propylene oxide and ethylene diamine. Other so-called nonionic detergent compounds include long-chain tertiary amine oxides and tertiary phosphine oxides.

Further suitable nonionic surfactants are alkyl polyglycosides of general formula

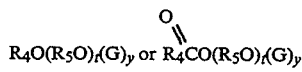

in which $R_4$ is an organic hydrophobic residue containing 10 to 20 carbon atoms, $R_5$ contains 2 to 4 carbon atoms, G is a saccharide residue containing 5 to 6 carbon atoms, t is in the range 0 to 25 and y is in the range from 1 to 10.

Alkyl polyglycosides of formula $R_4O(G)_y$, i.e. a formula as given above in which t is zero, are available from Horizon Chemical Co.

Other suitable nonionic surfactants include O-alkanoyl glucosides described in International Patent Application WO 88/10147 (Novo Industri A/S). Further possible hydrophobic nonionic surfactants are monoglyceryl ethers or esters of the respective formulae

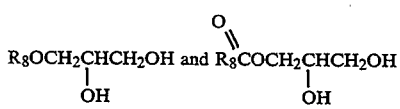

$R_8$ is preferably a saturated or unsaturated aliphatic residue.

The monoglyceryl ethers of alkanols are known materials and can be prepared, for example, by the condensation of a higher alkanol and glycidol. Glycerol monoesters are, of course, well known and available from various suppliers including Alkyril Chemicals Inc.

Other nonionic materials are the alkyl methyl sulphoxides and alkyl hydroxyethyl sulphoxides wherein the alkyl chain is $C_{10-14}$.

Detergency Builders

The bleaching detergent composition of the invention will generally contain one or more detergency builders, suitably in an amount of from 5 to 80 wt%, preferably from 20 to 80 wt%. This may be any material capable of reducing the level of free calcium ions in the wash liquor and will preferably provide the compositions with other beneficial properties such as the generation of an alkaline pH and the suspension of soil removed from the fabric.

Preferred builders include alkali metal (preferably sodium) aluminosilicates, which may suitably be incorporated in amounts of from 5 to 60% by weight (anhydrous basis) of the composition, and may be either crystalline or amorphous or mixtures thereof.

Examples of phosphorus-containing inorganic detergency builders include the water-soluble salts, especially alkali metal pyrophosphates, orthophosphates, polyphosphates and phosphonates. Specific examples of inorganic phosphate builders include sodium and potassium tripolyphosphates, orthophosphates and hexametaphosphates. Preferably, such inorganic phosphate builders are present at levels of not more than 5 wt% of the composition.

Other builders may also be included in the detergent composition of the invention if necessary or desired: suitable organic or inorganic water-soluble or water-insoluble builders will readily suggest themselves to the skilled detergent formulator. Inorganic builders that may be present include alkali metal (generally sodium) carbonate; while organic builders include polycarboxylate polymers such as polyacrylates, acrylic/maleic copolymers, and acrylic phosphinates; monomeric polycarboxylates such as citrates, gluconates, oxydisuccinates, glycerol mono-, di- and trisuccinates, carboxymethyloxysuccinates, carboxymethyloxymalonates, dipicolinates, hydroxyethyl iminodiacetates; and organic precipitant builders such as alkyl- and alkenylmalonates and succinates, and sulphonated fatty acid salts.

Especially preferred supplementary builders are polycarboxylate polymers, more especially polyacrylates and acrylic/maleic copolymers, suitably used in amounts of from 0.5 to 15 wt% and monomeric polycarboxylates, more especially citric acid and its salts, suitably used in amounts of from 3 to 20wt%.

Other Ingredients

It is desirable that the compositions according to the invention be approximately neutral or at least slightly alkaline, i.e. when the composition is dissolved in an amount to give surfactant concentration of 1 g/l in distilled water at 25° C., the pH should desirably be at least 7.5. For solid compositions the pH will usually be greater, such as at least 9. To achieve the required pH, the compositions may include a water-soluble alkaline salt.

This salt may be a detergency builder (as described above) or a non-building alkaline material.

Apart from the components already mentioned, the detergent compositions of the invention may contain any of the conventional additives in amounts in which such materials are normally employed in fabric washing detergent compositions. Examples of these components include lather boosters such as alkanolamides, particularly the monoethanolamides derived from palm kernel fatty acids and coconut fatty acids, lather depressants such as alkyl phosphonates and silicones, anti-redeposition agents such as sodium carboxymethyl cellulose and alkyl or substituted alkyl cellulose ethers; heavy metal sequestrants such as ethylene diamine tetraacetic acid and the phosphonic acid derivatives (i.e. Dequest ® types), fabric softening agents such as fatty amines, fabric softening clay materials; inorganic salts such as sodium and magnesium sulphate; and, usually present in very small amounts, fluorescent agents, perfumes, enzymes such as cellulases, lipases, amylases and oxidases, germicides, colorants or coloured speckles and pigments.

Other optional, but highly desirable components ingredients which may be employed in the detergent composition of the invention include polymers containing carboxylic or sulphonic acid groups in acid form or wholly or partially neutralised to sodium or potassium salts, the sodium salts being preferred.

Preferably, the polymeric material is present at a level of from 0.1 to about 3% by weight and has a molecular weight of from 1000 to 2,000,000 and may be a homo- or co-polymer of acrylic acid, maleic acid or salt or anhydride thereof, vinyl pyrrolidone, methyl or ethyl-vinyl ethers and other polymerisable vinyl monomers. Especially preferred materials are polyacrylic acid or polyacrylate, polymaleic acid/acrylic acid coplymer; 70:30 acrylic acid/hydroxyethyl maleate copolymer, 1:1 styrene/maleic acid coplymer; isobutylene/maleic acid and diisobutylene/maleic acid copolymers; methyl- and ethyl-vinylether/maleic acid copolymers; ethylene/maleic acid copolymer; polyvinyl pyrrolidone; and vinyl pyrrolidone/maleic acid copolymer. Other polymers which are especially preferred for use in liquid detergent compositions are deflocculating polymers such as, for example, disclosed in EP 346 995.

It may also be desirable to include in the detergent composition of the invention an amount of an alkali metal silicate, particularly sodium ortho-, meta- or preferably neutral or alkaline silicate, at a level of, for example, of 0.1 to 10 wt%.

The cationic peroxyacids of the present invention may be used in a variety of product forms including powders, on sheets or other substrates, in pouches, in tablets or in non-aqueous liquids, such as liquid nonionic detergent compositions.

When incorporated in a bleach and or detergent bleach composition, the cationic peroxyacids will preferably be in the form of particulate bodies comprising said cationic peroxyacid and a binder or agglomerating agent. In such a form, the cationic peroxyacid is more stable and easier to handle.

Many diverse methods for preparing such particulates have been described in various patents and patent applications such as, for example, GB 1 561 333; US 4 087 369; EP-A-0 240 057; EP-A-0 241 962; EP-A-0 101 634 and EEP-A-0 062 523, all of which are incorporated herein by reference. Any one of the methods described therein may be selected and used for preparing particulates comprising cationic acids of the invention.

When used in a detergent bleach composition, particulates incorporating the cationic peroxyacids of the invention are normally added to the base detergent powder in a dry-mixing process. However, it will be appreciated, the detergent base powder composition to which the peroxyacid particles are added may itself be made by any one of a variety of methods, such as spray-drying, high-energy mixing/granulation, dry-mixing, agglomeration, extrusion, flaking etc. Such methods are well known to those skilled in the art and do not form part of the present invention.

The cationic peroxyacids of the present invention may also be incorporated in detergent additive products. Such additive products are intended to supplement or boost the performance of conventional detergent compositions and may contain any of the components of such compositions, although they will not comprise all of the components present in a fully formulated detergent composition. Such additive products containing, for example, up to 90% by weight of the cationic peroxyacid and a surface-active material may be particularly useful in hygiene applications, e.g. hard surface cleaners.

Additive products in accordance with this aspect of the invention may comprise the cationic peroxyacid alone or in combination with a carrier, such as a compatible particulate substrate, a flexible non-particulate substrate or a container (e.g. pouch or sachet).

Examples of compatible particulate substrates include inert materials, such as clays and other aluminosilicates, including zeolites both of natural and synthetic of origin. Other compatible particulate carrier substrates include hydratable inorganic salts, such as phosphates, carbonates and sulphates.

Additive products enclosed in bags or containers can be manufactured such that the bags/containers prevent egress of their contents when dry but are adapted to release their contents on immersion in an aqueous solution.

In a further specific embodiment of the invention, the cationic peroxyacids of the invention may be suitably incorporated in so-called non-aqueous liquid detergent compositions, to impart an effective cleaning and stain-removing capacity to the liquid composition when used on fabrics and textiles.

Non-aqueous liquid detergent compositions, including paste-like and gelatinous detergent compositions, are known from the art and various formulations have been proposed, for example, in U.S. Pat. Nos. 2,864,770; 2,940,938; 4,772,412; 3,368,977; British Patents 1,205,711; 1,270,040; 1,292,352; 1,370,377; 2,194,536; DE-A-2,233,771; and EP-A-0,028,849.

Such liquid compositions typically comprise a non-aqueous liquid medium with or without a solid phase dispersed therein.

The non-aqueous liquid medium may be a liquid surfactant, preferably a liquid nonionic surfactant; a non-polar liquid medium, for example a liquid paraffin; a polar solvent, for example polyols such as glycerol, sorbitol, ethylene glycol, optionally combined with low-molecular monohydric alcohols, for example ethanol or isopropanol; or mixtures thereof.

The solid phase may be builders, alkalis, abrasives, polymers, clays, other solid ionic surfactants, bleaches, fluorescent agents and other generally solid detergent ingredients.

The invention is further illustrated by way of the following non-limiting examples.

EXAMPLES

Example I

Preparation of a methane sulphonic acid salt of 3-trimethyl ammonium-propyl-amido-4'-peroxybenzoic acid (5)

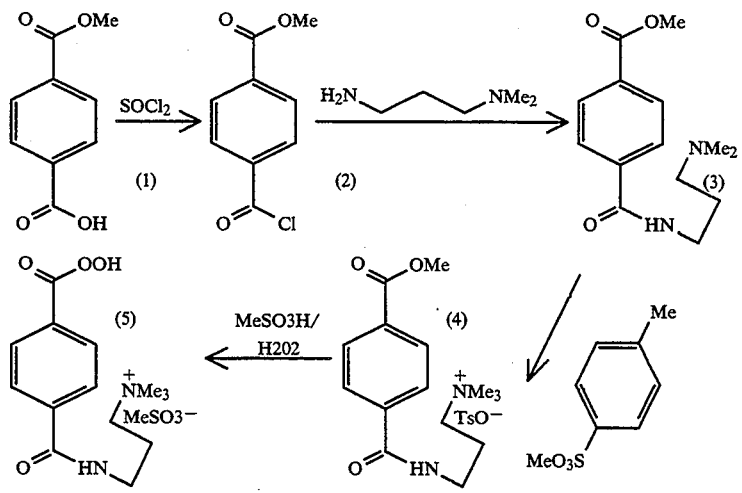

Monomethyl terephthalate (1) (20 g, 0.11 m) was dissolved in anhydrous chloroform (50 ml) and thionyl chloride (50 ml, xs) was added. The solution was stirred at room temperature for 5 h. The solvents were removed under reduced pressure to yield a white solid identified as acid chloride (2) (22 g, yield=99%). $vcm^{-1}$ 1780, 1730.

This acid chloride (2) (22 g, 0.11 m) was dissolved in dry acetonitrile (100 ml) and a solution of 3-dimethylaminopropylamine (11.32 g, 0.11 m) in acetonitrile (50 ml) was added dropwise, with stirring, while the temperature was maintained at 10° C. After the addition was completed the mixture was stirred for a further 5 h. A white precipitate formed which was removed by filtration and washed with cold acetonitrile to give a white solid identified as an amine salt (24.2 g yield=73%).($\delta D_2O$) 8.12, d, 2H, Ar-H; 7.88, d, 2H, Ar-H; 3.98, s, 3H COOMe; 3.53, t, 2H, $CH_2NHCO$; 3.22, t, 2H $CH_2N^+$; 2.95, s, 6H $NMe_2^+$; 2.1, p, 2H $CH_2CH_2N^+$.

This amine salt (24.2 g, 0.08 m) was partitioned between sodium hydroxide solution (41 ml 2M) and ethyl acetate (200 ml). The mixture was shaken until all solid was dissolved, separated and the ethyl acetate layer dried over anhydrous sodium sulphate. The solution was filtered, and the solvent removed to dryness under reduced pressure to yield an oil identified as the amino ester (3) (19.6 g, yield=92%).

This amino ester (3) (15 g, 0.56 m) was dissolved in acetonitrile (100 ml) and methyl-p-tolulene sulphonate (11.63 g, 0,625 m) and the mixture was heated under reflux for 4.5 h. The solvent was removed under reduced pressure to yield a sticky solid which was triturated with ether and recrystallised from acetonitrile to give white plates (20.1 g, yield=86%), identified as salt (4) $^1$Hnmr Assay (D$_2$O; trioxan)=99%, ($\delta D_2O$) 8.12, d, 2H, Ar-H; 7.88, d, 2H, Ar-H; 7.68, d, 2H ArH; 7.35, d, 2H ArH; 3.95, s, 3HCOOMe; 3.53, t, 2H $CH_2NHCO$; 3,42, t, 2H $CH_2N^+$; 3.16, s, 9H $NMe_3^+$; 2.4, s, 3H Ar-Me; 2.15, p, 2H $CH_2CH_2N^+$.

This salt (4) (4.47 g, 0.01 m) was dissolved in methane sulphonic acid (25 ml) to give a solution. This solution was cooled to 5° C. in an ice bath and hydrogen peroxide (1.7 g; 1.51 ml of 85%; 52 mM) was added dropwise over 30 mins. The resulting solution was allowed to reach room temperature and stirred for a further 4 h. This resulting mixture was poured into dried ether (Na) (400 ml) to precipitate a sticky solid which was further triturated with dried ether (2×50 ml), yielding a solid (4 g) . Titration=63% peracid; this solid was triturated with dried analar acetone (60 ml) to give a white solid (2 g, yield=53%) identified as (5). $^1$Hnmr Assay (D$_2$O; trioxan) =99%, ($\delta$D$_2$O) 8.05, d, 2H, Ar-H; 7.85, d, 2H, Ar-H; 3.53, t, 2H, CH$_2$NHCO; 3.42, t, 2H CH$_2$N$^+$; 3.16, s, 9H NMe$_3$$^+$; 2.8, s, 3H MeSO$_3$$^-$; 2.15, p, 2H CH$_2$CH$_2$N$^+$.

Example II, Comparative Example A

Bleaching experiments were carried out in a temperature-controlled glass vessel, equipped with a magnetic-stirrer, thermocouple and a pH electrode, at a constant temperature of 40° C. pH was adjusted, using 0.1M NaOH.

The peracid (1×10$^{-3}$ M) prepared according to example I was added to 100 ml demineralised water in the glass vessel. Thereafter, tea-stained test cloths were immersed in the solution for 30 minutes. The liquor to cloth ratio was greater than 20:1. After rinsing with tap water, the cloths were dried in a tumble drier.

For reasons of comparison, a peracid having the formula Me$_3$N-CH$_2$-CO$_3$H HSO$_4$$^-$ and prepared according to Example 3 of EP-A-316 809 was also tested, using the above method.

Bleaching performance of both types of peracid was determined, using a Instrumental Colour Systems Micro-match to measure the reflectance, at 460 nm, of the cloths both before and after treatment. The difference ($\Delta$R$_{460}$*) in the values gives a measure of the effectiveness of the treatment. The results in terms of this reflectance difference, are given below:

| Example | Peracid | pH 7.0 | pH 10.0 |
| --- | --- | --- | --- |
| II | Compound of Example 1 | 30.8 | 20.6 |
| A | peracid of prior art | 15.0 | 8.6 |

It can be seen that at both pH values the compound according to the invention gives a considerably better bleaching performance than the prior art compound.

Example III

Preparation of a toluene sulphonic acid salt of 4(3'-N Hexyl.N.N-dimethyl ammonium propylamido) peroxy benzoic acid which is a compound of formula (III), see below.

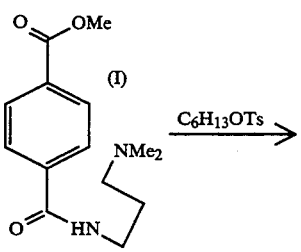

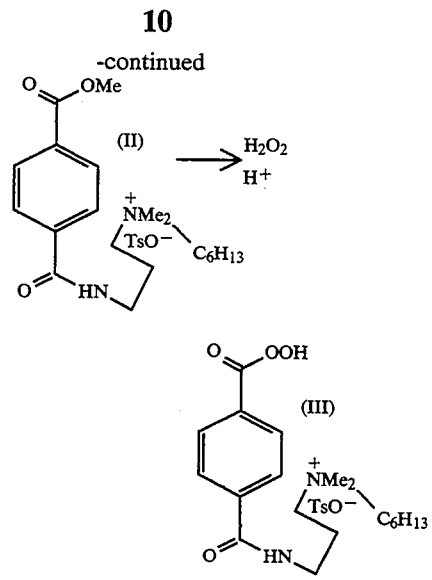

An amino ester having the formula (I) (see above) was prepared according to the method as described in Example I. This amino ester (13.2 g, 0.05 m) was dissolved in acetonitrile (150 m%) and hexyl tosylate (16 g, 0.055 m) was added. The solution was heated under reflux for a period of 3 h. The mixture was left to cool and a white solid identified as salt (II) (see above) crystallised out of solution (19 g, yield=73%) $^1$Hnmr Assay (D$_2$O/DMSO trioxan)=98.6%, ($\delta$D$_2$O/DMSO) 8.15, d, 2H ArH; 7.95, d, 2H ArH; 7.58, d, 2H ArH; 7.25, d, 2H ArH; 3.95, s, 3H COOMe; 3.45, t, 2H, CH$_2$NHCO; 3.36, t, 2H CH$_2$N$^+$; 3.17,t, 2H CH$_2$N$^+$; 3.04, s, 6H N$^+$Me$^2$; 2.4, s, 3H Ar-Me; 2.03,m, 2H CH$_2$CH$_2$N$^+$; 1.65, m, 2H CH$_2$CH$_2$N$^+$; 1.3, m, 6H (CH$_2$)$_3$; 0.85, t, 3H (CH$_2$)$_3$-CH$_3$.

This salt (II) (3.0 g, 0.0057 m) was dissolved in methane sulphonic acid (7.5 g) to give a solution. This solution was cooled to 3°-5° C. in an ice bath and hydrogen peroxide (85%; 0.58 g, 0.017 m) was added dropwise over a period of 3 mins with a temperature rise of 2° C. The resulting solution was left stirring at 6° C. for a further 44 minutes, then heated to 36° C. for 6 hours. This mixture was added to an aqueous solution of toluene sulphonic acid (1.31 g in 100 ml water), a precipitate formed was removed by filtration and dried in vacuo to give a white solid (2.34 g; yield=78%) ml), identified as (III). $^1$Hnmr Assay (D$_2$O/DMSO; trioxan)=95.6% quat salt (of which 16% ester), ($\delta$D$_2$O/DMSO) 8.15, d, 2H, Ar-H; 7.9, d, 2H, Ar-H;7.6, d, 2H ArH; 7.38, d, 2H ArH; 3.95, s, 3H COOMe; 3.45, t, 2H, CH$_2$NCO; 3.36, t, 2H CH$_2$N$^+$; 3.17, t, 2H CH$_2$N$^+$; 3.04 s 6H N$^+$Me$_2$; 2.4, s, 3H ArMe; 2.03, m, 2H CH$_2$CH$_2$N$^+$; 1.65, m 2H CH$_2$CH$_2$N$^+$; 1.3, m, 6H(CH$_2$)$_3$; 0.85, t, 3H (CH$_2$)$_3$-CH$_3$. Percentage peracid by titration: 77%

Example IV

Bleaching experiments were carried out, using the method of Example II, whereby the bleaching performance of the peracid prepared according to Example III was tested.

The reflectance difference values found were the following:

At a pH of 7.0: 29.1
At a pH of 10.0: 16.3

It can be seen that the bleaching performance in this case is somewhat worse than the performance found in Example II. This is caused by the somewhat reduced solubility of the bleaching compound tested due to the long alkyl chain present therein.

We claim:

1. A bleaching detergent composition comprising: from 3 to 40% by weight of at least one surface-active compound; from 5 to 80% by weight of at least one detergency builder; and an effective amount for bleaching of a cationic peroxyacid of formula (I)

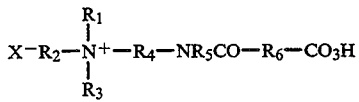

wherein:
$R_1$ is a $C_1$-$C_8$ radical selected from alkyl, alkenyl and alkylaryl groups;
$R_2$ and $R_3$ are each a $C_1$-$C_3$ alkyl group;
$R_4$ is $(CH_2)_n$, where n is an integer from 1 to 7;
$R_5$ is hydrogen;
$R_6$ is phenyl; and
$X^-$ is a counter anion.

2. Composition according to claim 1, wherein the cationic peroxyacid is present at a concentration of from 0.5 to 15% by weight.

3. A cationic peroxyacid of formula (I)

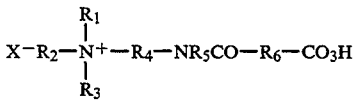

wherein:
$R_1$ is a $C_1$-$C_8$ radical selected from alkyl, alkenyl and alkylaryl groups;
$R_2$ and $R_3$ are each a $C_1$-$C_3$ alkyl group;
$R_4$ is $(CH_2)_n$, where n is an integer from 1 to 7;
$R_5$ is hydrogen;
$R_6$ is phenyl; and
$X^-$ is a counter anion.

4. Peroxyacid according to claim 3, wherein $R_6$ is aryl and the -$CO_3H$ is in the para or meta position.

5. Peroxyacid according to claim 3, wherein
$R_1$ is a $C_1$-$C_6$ alkyl group; and
$R_4$ is a $(CH_2)_3$.

* * * * *